(12) United States Patent
Mueller et al.

(10) Patent No.: US 11,226,303 B2
(45) Date of Patent: Jan. 18, 2022

(54) GAS SENSOR FOR MEASURING A CONCENTRATION OF AN ANALYSIS GAS

(71) Applicant: Robert Bosch GmbH, Stuttgart (DE)

(72) Inventors: Renate Mueller, Reutlingen (DE); Tobias Sebastian Frey, Ludwigsburg (DE)

(73) Assignee: Robert Bosch GmbH, Stuttgart (DE)

( * ) Notice: Subject to any disclaimer, the term of this patent is extended or adjusted under 35 U.S.C. 154(b) by 69 days.

(21) Appl. No.: 16/642,598

(22) PCT Filed: Aug. 16, 2018

(86) PCT No.: PCT/EP2018/072171
§ 371 (c)(1),
(2) Date: Feb. 27, 2020

(87) PCT Pub. No.: WO2019/048202
PCT Pub. Date: Mar. 14, 2019

(65) Prior Publication Data
US 2020/0348252 A1 Nov. 5, 2020

(30) Foreign Application Priority Data
Sep. 5, 2017 (DE) .......................... 102017215527.2

(51) Int. Cl.
*G01N 27/18* (2006.01)
*G01N 33/00* (2006.01)
*G01N 25/18* (2006.01)

(52) U.S. Cl.
CPC ............. *G01N 27/18* (2013.01); *G01N 25/18* (2013.01); *G01N 33/0009* (2013.01); *G01N 33/0027* (2013.01); *G01N 33/0062* (2013.01)

(58) Field of Classification Search
CPC .... G01N 25/18; G01N 27/18; G01N 33/0004; G01N 33/0009; G01N 33/0027; G01N 33/0062
See application file for complete search history.

(56) References Cited

U.S. PATENT DOCUMENTS

| 6,840,103 B2 | 1/2005 | Lee et al. |
| 2005/0006236 A1 | 1/2005 | Kim et al. |

(Continued)

FOREIGN PATENT DOCUMENTS

| DE | 102016200258 A1 | 7/2017 |
| DE | 102016200267 A1 | 7/2017 |

(Continued)

OTHER PUBLICATIONS

International Search Report for PCT/EP2018/072171, dated Oct. 5, 2018.

(Continued)

*Primary Examiner* — Benjamin R Schmitt
(74) *Attorney, Agent, or Firm* — Norton Rose Fulbright US LLP; Gerard Messina

(57) ABSTRACT

A gas sensor is described for measuring a concentration of an analysis gas based on a thermal conductivity principle, including at least one analysis heating element situated on a first diaphragm for heating the analysis gas, a reference heating element situated on a second diaphragm for heating a reference gas, at least one evaluation electronics unit for measuring a resistance change of the analysis heating element caused by the analysis gas in relation to an electrical resistance of the reference heating element, the first diaphragm and the second diaphragm being situated adjacent to one another in a sensor substrate, due to a base substrate situated on one side on the sensor substrate, a measuring volume is formable between the first diaphragm and the base (Continued)

substrate and a reference volume is formable between the second diaphragm and the base substrate.

13 Claims, 1 Drawing Sheet

(56) References Cited

U.S. PATENT DOCUMENTS

| | | | |
|---|---|---|---|
| 2005/0025215 A1* | 2/2005 | Arndt | G01N 25/18 374/44 |
| 2005/0265422 A1 | 12/2005 | Bonne | |
| 2012/0042712 A1* | 2/2012 | Kishi | G01N 30/66 73/23.35 |

FOREIGN PATENT DOCUMENTS

| | | |
|---|---|---|
| DE | 102016200270 A1 | 7/2017 |
| EP | 2431737 A1 | 3/2012 |
| JP | H08110317 A | 4/1996 |
| JP | 2004037235 A | 2/2004 |
| JP | 2005337896 A | 12/2005 |
| JP | 2010237007 A | 10/2010 |
| JP | 2017036936 A | 2/2017 |

OTHER PUBLICATIONS

De Graaf G., et al., "Micro Thermal Conductivity Detector With Flow Compensation Using a Dual MEMS Device", Sensors and Actuators A: Physical, Elsevier BV, NL, BD. 249, 2016, pp. 186-198, XP029743283.

* cited by examiner

GAS SENSOR FOR MEASURING A CONCENTRATION OF AN ANALYSIS GAS

FIELD

The present invention relates to a gas sensor for measuring a concentration of an analysis gas based on a thermal conductivity principle, including at least one analysis heating element situated on a first diaphragm for heating the analysis gas, a reference heating element situated on a second diaphragm for heating a reference gas, and at least one evaluation electronics unit for measuring a resistance change of the analysis heating element caused by the analysis gas in relation to an electrical resistance of the reference heating element.

BACKGROUND INFORMATION

In gas sensors which operate according to resistive measurement principles, the gas or gas mixture to be measured directly influences the conductivity of a gas-sensitive sensor element. This resistance change is used as a measured variable for a concentration of the gas or gas mixture. The gas-sensitive sensor element may be a sensor layer or a heating element in this case. For example, one or multiple heating element(s) in the form of platinum heaters may be situated on a diaphragm. These heating elements may be operated using constant current or using constant power and may be warmer than an ambient temperature.

To measure a hydrogen concentration, for example, the better thermal conductivity of hydrogen of 1810 $\mu$W/cmK in relation to the thermal conductivity of air of 260 $\mu$W/cmK may be utilized. If hydrogen is located in the surroundings of the heating element, the temperature of the heating element thus drops due to the higher thermal conductivity of the hydrogen and a greater heat dissipation accompanying this, and the resistance of the heating element is thus reduced. This resistance change or the additional heating power which has to be applied to keep the heating element at a constant temperature is proportional to the concentration of the hydrogen. Since the thermal conductivity is dependent on the ambient temperature, the ambient temperature may be measured with the aid of a further temperature sensor, for example.

The resistance of the heating element changes due to the temperature coefficient of the material of the heating element in the event of a change of the ambient temperature or due to different operating voltages. For example, hydrogen may be differentiated from ambient humidity with the aid of suitable evaluation algorithms.

In order that a gas sensor may measure a concentration of a gas reliably and precisely, a change of the electrical resistance of the heating element in the event of changes of the ambient temperature, the ambient humidity, and different operating voltages has to be taken into consideration. This may result in a complex evaluation electronics unit and larger dimensions of the sensor.

SUMMARY

An object of the present invention includes providing a compact gas sensor, which may carry out precise concentration measurements of at least one gas regardless of external conditions or aging effects.

This object may achieved with the aid of the present invention. Advantageous embodiments of the present invention are described herein.

According to one aspect of the present invention, an example gas sensor is provided for measuring a concentration of an analysis gas based on a thermal conductivity principle. The gas sensor includes at least one analysis heating element situated on a first diaphragm for heating the analysis gas. A reference heating element for heating a reference gas is situated on a second diaphragm. An evaluation electronics unit is used for measuring a resistance change of the analysis heating element caused by the analysis gas in relation to an electrical resistance of the reference heating element. According to the present invention, the first diaphragm and the second diaphragm are situated adjacent to one another in a sensor substrate, whereby due to a base substrate situated on one side at the sensor substrate, a measuring volume is formable between the first diaphragm and the base substrate and a reference volume is formable between the second diaphragm and the base substrate.

To enable dimensions of the gas sensor or a chip surface of the gas sensor, an additional wafer or a base substrate is applied to the lower side of the sensor substrate to thus generate a reference volume, in which no or only a defined quantity of hydrogen gas or water vapor or a reference gas is introduced. Due to the use of the gas sensor as a double diaphragm chip including a capped reference volume with respect to the gas to be detected, in particular the dimensions of the gas sensor may be reduced. A lower side of the base substrate may be used, for example, as a joining surface or as a substrate for further functionalities.

Due to the use of a reference volume, manufacturing-related variations in the resistance may be compensated for, since the variations apply equally to the reference volume and the measuring volume. This relationship may result in particular from joint and nearly simultaneous manufacturing of both components of the gas sensor. As a result of the direct arrangement of the first diaphragm to the second diaphragm, the heating elements are also equally affected by these variations. Furthermore, temperature changes and changes of further parameters, for example, moisture, may act directly on both heating elements of both volumes, so that deviations in boundary conditions of a reference measurement and an analysis measurement do not have to be taken into consideration by the evaluation electronics unit. The sensor substrate may be made up of a doped or undoped semiconductor, for example, silicon, a glass, a plastic, or a ceramic.

According to one specific example embodiment of the gas sensor, the measuring volume and/or the reference volume are formed at least in areas within the sensor substrate and/or at least partially within the base substrate. For example, a reference volume and a measuring volume may be introduced into the sensor substrate by material removal and may be at least in areas closed using a base substrate. Alternatively or additionally, the reference volume and/or the measuring volume may protrude at least regionally into the base substrate.

According to a further specific embodiment of the gas sensor, the reference volume is an open volume or a closed volume. For example, the reference volume may be fluidically connected by an opening in the second diaphragm to adjacent surroundings. Alternatively, the reference volume may be closed and may include a defined reference gas. In this way, concentration measurements of an analysis gas may be carried out more precisely.

According to a further specific embodiment of the gas sensor, the analysis gas is introducible into the measuring volume through at least one opening in the base substrate. In a simplest specific embodiment, the analysis gas may be introduced via a borehole into the measuring volume. In addition, inlet and outlet openings may be used for a continuous through flow of an analysis gas. The openings may be introduced into the base substrate, for example, by etching processes, trenching processes, lasers, milling, or drilling. The at least one opening may be formed structured and optimized for flow in this case. In particular, the at least one opening may be formed in such a way that the at least one opening forms particle, moisture, and water protection for the measuring volume. For this purpose, for example, a water-repellent coating of the at least one opening may reduce the adhesion of ambient moisture. The at least one opening may be dimensioned and formed in such a way that a gas flow through the at least one opening is laminar. In this way, reproducible, defined boundary conditions for the thermal conduction equation or heat sink of the heating elements of the gas sensor may be implemented. Furthermore, the comparability and reproducibility of the measuring results may be increased in this way.

According to a further specific embodiment of the gas sensor, at least one heating element may be applied into or onto the base wafer. In this way, the base substrate may be additionally functionalized. For example, additional heating elements or heater tracks may be used for heating of the reference volume and/or the measuring volume. In this way, the gas sensor may be brought to an operating temperature faster or deiced. Furthermore, condensation of ambient moisture in the measuring volume may be prevented by additional heating. In the case of a ceramic substrate, a sintered heating coil or a heating coil printed on via a thick-film method may be used for high powers. The reference volume and the measuring volume may also be kept at an equal temperature by additional heating elements and the comparability may thus be increased. At low heating powers, a silicon substrate or a glass substrate having a platinum resistor heating element may be used. Alternatively, doped semiconductors, for example, silicon carbonate having a resistor heating element made of tungsten, silver, gold, copper, or aluminum may also be used.

According to a further specific embodiment of the gas sensor, at least one gas filter is situated in the measuring volume. The measuring volume may be coated using a functional layer. The functional layer may be, for example, a getter material, which may at least temporarily bond specific undesirable gases or particles. In this way interfering components or components which corrupt a measurement in the analysis gas may be filtered out.

According to a further specific embodiment of the gas sensor, at least one gas filter is situated on one side on the base substrate. A special functionalized layer may be applied to the base substrate to filter specific gas types. In this way, it is possible to prevent undesirable gases from being able to pass through the at least one opening into the measuring volume and thus to the first diaphragm. For example, specific gases may react on a getter layer and may be introduced, for example, into a solid structure. Alternatively or additionally, the gas filter may span or cover the at least one opening of the measuring volume, for example, to prevent the penetration of water vapor or other undesirable gases or particles. A separation of water and hydrogen may be ensured in this way.

According to a further specific embodiment of the gas sensor, the base substrate is connectable via a joining means to the sensor substrate. The base substrate may be situated on the sensor substrate, for example, by a glass frit bond, an anodic bond, a eutectic bond, or by a soldered bond or an adhesive bond. The base substrate may thus be connected by a variety of possible methods to the sensor substrate.

According to a further specific embodiment of the gas sensor, the base substrate includes a joining surface on one side for accommodating an adhesive or a sealant. Due to the reduced dimensions of the gas sensor and the high level of plane-parallelism of the substrates, a lower side of the base substrate may be used as a joining surface. In particular, the base substrate may be adhesively bonded or sealed for effective sealing against ambient moisture and other environmental influences.

According to a further specific embodiment of the gas sensor, a cap substrate is situated on a side of the sensor substrate opposite to the base substrate. To increase a mechanical stability of the gas sensor, an additional cap substrate may be situated on the sensor substrate. In particular, the cap substrate may already be situated beforehand on the sensor substrate to provide a stable foundation for further processing steps for manufacturing the gas sensor. The cap substrate preferably includes recesses in the area of the first diaphragm and the second diaphragm. The recesses may have been introduced by material removal into the cap substrate, for example, just like the reference volume and the measuring volume.

According to a further specific embodiment of the gas sensor, at least one part of the evaluation electronics unit is situated on or in the cap substrate. The cap substrate may be used to accommodate electrical strip conductors and electrical components. The gas sensor may be designed particularly compactly in this way. In particular, an external evaluation electronics unit may be omitted in this way. For example, silicon vias, wire bonds, and trenches may be introduced into the cap substrate and the sensor substrate to form the evaluation electronics unit. Furthermore, an additional heating element may also be introduced into or onto the cap substrate. Alternatively or additionally, an evaluation electronics unit may be situated at least partially in or on the base substrate.

According to a further specific embodiment of the gas sensor, the cap substrate includes at least one connecting opening to the reference volume. In this way, the reference volume may be designed to be open in order to be able to carry out a pressure equalization with surroundings of the gas sensor.

Preferred exemplary embodiments of the present invention are explained in greater detail hereafter on the basis of greatly simplified schematic views.

DETAILED DESCRIPTION OF EXAMPLE EMBODIMENTS

Figure 1:
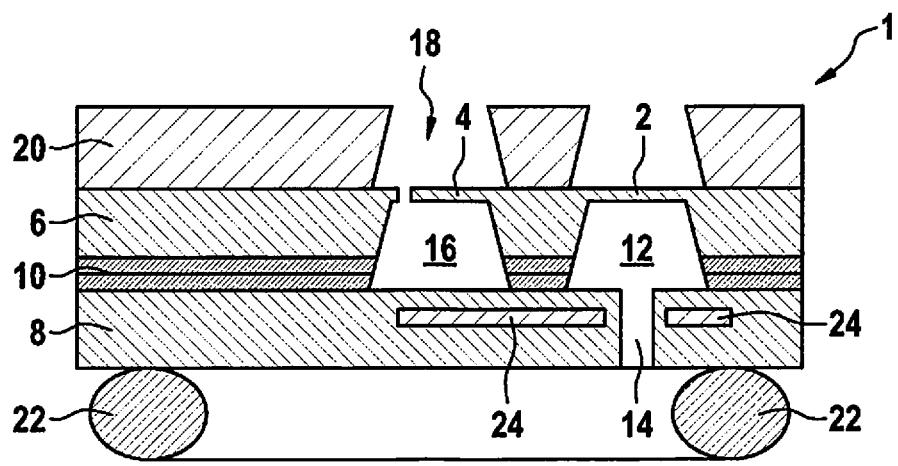
FIG. 1 shows a schematic view of a gas sensor according to a first exemplary embodiment.

In the figures, the same design elements each have the same reference numerals.

FIG. 1 shows a schematic view of a gas sensor 1 according to a first exemplary embodiment. Gas sensor 1 includes a first diaphragm 2 and a second diaphragm 4. An analysis heating element is situated on first diaphragm 2. A reference heating element is positioned on second diaphragm 4. First diaphragm 2 and second diaphragm 4 are formed by material removal of sensor substrate 6. A base substrate 8 is fastened via a joining means 10 on a lower side of sensor substrate 6. A measuring volume 12 is enclosed between first diaphragm 2 and base substrate 8. An analysis gas may be conducted into measuring volume 12 and analyzed via an opening 14.

A reference volume 16 is formed between second diaphragm 4 and base substrate 8. A fluidic connection between reference volume 16 and surroundings of gas sensor 1 exists via an opening 18 in second diaphragm 4. In this way, for example, a pressure equalization in reference volume 16 may be enabled. A cap substrate 20 is situated on an upper side of sensor substrate 6. Cap substrate 20 includes recesses in the area of first diaphragm 2 and second diaphragm 4. A sealant 22 for sealing opening 14 from the surroundings of gas sensor 1 is applied to a lower side of base substrate 8. An additional heating element 24 for heating reference volume 16 and measuring volume 12 is integrated into base substrate 8.

Figure 2:
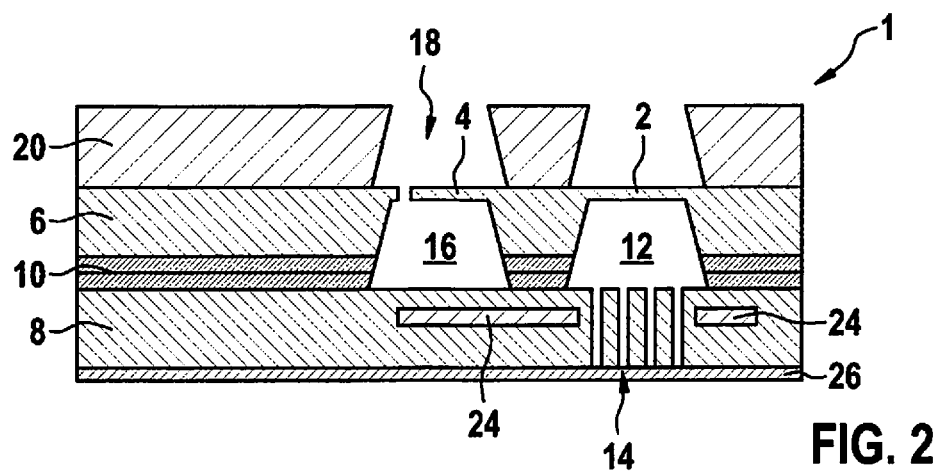
FIG. 2 shows a schematic view of a gas sensor according to a second exemplary embodiment.

FIG. 2 shows a schematic view of a gas sensor 1 according to a second exemplary embodiment. In contrast to gas sensor 1 according to the first exemplary embodiment, the lower side of base substrate 8 is coated using a gas filter 26. Gas filter 26 covers supply line 14 of a gas to be analyzed into measuring volume 12 in this case. In this way, for example, a penetration of water vapor into measuring volume 12 may be prevented. Supply line 14 is formed according to the exemplary embodiment in the form of four openings situated in parallel to one another.

Figure 3:
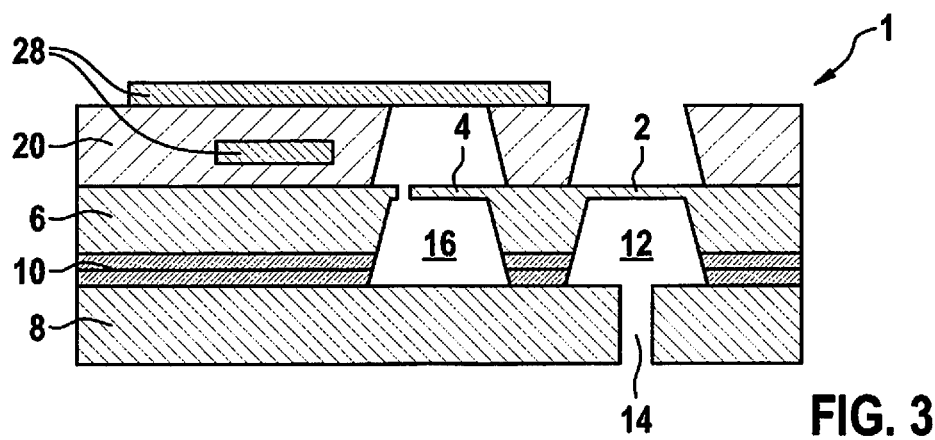
FIG. 3 shows a schematic view of a gas sensor according to a third exemplary embodiment.

FIG. 3 shows a schematic view of a gas sensor 1 according to a third exemplary embodiment. In contrast to gas sensor 1 according to the first exemplary embodiment and gas sensor 1 according to the second exemplary embodiment, gas sensor 1 according to the third exemplary embodiment includes a closed reference volume 16. A reference gas is enclosed in reference volume 16, which may be used for comparison during a measurement of an analysis gas in measuring volume 12. Reference volume 16 is closed here by cap substrate 20.

According to the exemplary embodiment, cap substrate 20 includes an electronic circuit 28 situated on cap substrate 20. One part of electronic circuit 28 is integrated into cap substrate 20. Electronic circuit 28 forms an evaluation electronics unit 28 in this case. Evaluation electronics unit 28 applies a defined voltage and a defined current to the reference heating element situated on second diaphragm 4 and the analysis heating element situated on first diaphragm 2 for setting a defined temperature.

By introducing an analysis gas into measuring volume 12, the heat of the analysis heating element, for example, may be dissipated faster, so that a heating power has to be increased by evaluation electronics unit 28 to be able to maintain the defined temperature. A concentration of a gas to be measured in measuring volume 12 may be ascertained on the basis of a comparison of the required heating power of reference volume 16 and the heating power of measuring volume 12.

What is claimed is:

1. A gas sensor for measuring a concentration of an analysis gas based on a thermal conductivity principle, comprising:
    at least one analysis heating element, situated on a first diaphragm, to heat the analysis gas;
    a reference heating element, situated on a second diaphragm, to heat a reference gas;
    at least one evaluation electronics unit to measure a resistance change of the analysis heating element caused by the analysis gas in relation to an electrical resistance of the reference heating element;
    wherein the first diaphragm and the second diaphragm are situated adjacent to one another in a sensor substrate of the gas sensor, due to a base substrate situated on one side at the sensor substrate, a measuring volume being formable between the first diaphragm and the base substrate and a reference volume being formable between the second diaphragm and the base substrate, the reference volume being fluidically connected to an adjacent surroundings via an opening in the second diaphragm,
    wherein the second diaphragm of the reference volume and the first diaphragm of the measuring volume lie in a top plane, below which are the reference volume and the measuring volume, and wherein bottoms, opposite the diaphragms, of the volumes are in a bottom plane parallel to the top plane,
    wherein the base substrate is fastened via a joining means on a lower side of the sensor substrate, and
    wherein a cap substrate is situated on a side of the sensor substrate opposite to the base substrate.

2. The gas sensor as recited in claim 1, wherein the measuring volume and/or the reference volume is formed at least in areas within the sensor substrate and/or is formed at least partially within the base substrate.

3. The gas sensor as recited in claim 1, wherein the analysis gas is introducible through at least one opening in the base substrate into the measuring volume.

4. The gas sensor as recited in claim 1, further comprising:
    at least one additional heating element applied in or on the base substrate.

5. The gas sensor as recited in claim 1, further comprising:
    at least one gas filter situated in the measuring volume.

6. The gas sensor as recited in claim 1, further comprising:
    at least one gas filter situated on one side on the base substrate.

7. The gas sensor as recited in claim 1, wherein the base substrate includes a joining surface on one side accommodating an adhesive or a sealant.

8. The gas sensor as recited in claim 1, wherein at least one part of the evaluation electronics unit is situated on or in the cap substrate.

9. The gas sensor as recited in claim 1, wherein the cap substrate includes at least one connecting opening to the reference volume.

10. The gas sensor as recited in claim 1, wherein the reference volume is closed by the cap substrate.

11. The gas sensor as recited in claim 1, wherein the reference volume is closed by the cap substrate, and wherein the cap substrate includes an evaluation electronic circuit situated on the cap substrate and a part of the evaluation electronic circuit is integrated into the cap substrate.

12. The gas sensor as recited in claim 11, wherein the evaluation electronics unit applies a defined voltage and a defined current to the reference heating element situated on the second diaphragm and the analysis heating element situated on the first diaphragm for setting a defined temperature.

13. The gas sensor as recited in claim 12, wherein an analysis gas is introduced into the measuring volume, so as to dissipate faster a heat of the analysis heating element, so that a heating power is increased by the evaluation electronics unit to maintain a defined temperature, and wherein a concentration of a gas to be measured in the measuring volume is ascertained based on a comparison of a required heating power of the reference volume and the heating power of the measuring volume.

* * * * *